United States Patent
Ribi

(10) Patent No.: US 6,866,863 B2
(45) Date of Patent: *Mar. 15, 2005

(54) INGESTIBLES POSSESSING INTRINSIC COLOR CHANGE

(75) Inventor: Hans O. Ribi, Hillsbrough, CA (US)

(73) Assignee: Segan Industries, Inc., Burlingame, CA (US)

( * ) Notice: Subject to any disclaimer, the term of this patent is extended or adjusted under 35 U.S.C. 154(b) by 100 days.

This patent is subject to a terminal disclaimer.

(21) Appl. No.: 10/355,720

(22) Filed: Jan. 31, 2003

(65) Prior Publication Data

US 2003/0143188 A1 Jul. 31, 2003

Related U.S. Application Data

(62) Division of application No. 09/602,001, filed on Jun. 23, 2000, now Pat. No. 6,607,744.

(51) Int. Cl.[7] .......................... A61K 47/00; A61K 9/20; A61K 9/44; A61K 7/16
(52) U.S. Cl. ..................... 424/439; 424/464; 424/467; 424/49
(58) Field of Search ............................... 424/439, 464, 424/467, 49

(56) References Cited

U.S. PATENT DOCUMENTS

| | | |
|---|---|---|
| 3,309,274 A | 3/1967 | Brilliant |
| 4,238,352 A | 12/1980 | Patel |
| 4,339,951 A | 7/1982 | Yee et al. |
| 4,721,769 A | 1/1988 | Rubner |
| 4,737,463 A | 4/1988 | Bhattacharjee |
| 4,847,066 A | 7/1989 | Honigs et al. |
| 4,859,538 A | 8/1989 | Ribi et al. |
| 5,144,112 A | 9/1992 | Wyatt et al. |
| 5,156,810 A | 10/1992 | Ribi et al. |
| 5,189,281 A | 2/1993 | Wyatt et al. |
| 5,273,360 A | 12/1993 | Wyatt et al. |
| 5,415,999 A | 5/1995 | Saul et al. |
| 5,685,641 A | 11/1997 | Ribi et al. |
| 5,788,375 A | 8/1998 | Parker et al. |
| 5,918,981 A | 7/1999 | Ribi et al. |
| 6,046,455 A | 4/2000 | Ribi et al. |
| 6,183,772 B1 | 2/2001 | Charych et al. |
| 6,277,652 B1 * | 8/2001 | Jo et al. ..................... 436/518 |

OTHER PUBLICATIONS

Campbell et al. Coulombic screening in polydiacetylene crystals. Polymer, 1995, 36(4), 675–89.*

Lim K et al.Positron trap states in amorphous and crystalline conjugated polydiacetylene polymers, Physics Letters A (1989), 142(2–3), 164–168.*

Ma Zhanfang et al., Color–changeable vesicles of polydiacetylenic matrix incorporating glycolipid based on physical force. Acta Physico–Chimica Sinica, 15(2):101–104, Feb. 1999.*

"Food Facts", U.S. Food and Drug Administration, Brochure: Jan. 1993, pp. 1–6.*

Ma et. al., Journal of the American Chemical Society, vol. 120, pp. 12678–12679, 1998.

* cited by examiner

Primary Examiner—Thurman K. Page
Assistant Examiner—Lakshmi Channavajjala
(74) Attorney, Agent, or Firm—Bret E. Field; Bozicevic, Field & Francis LLP

(57) ABSTRACT

Methods and compositions are provided comprising ingestibles and a thermochromic composition which is informative as to the temperature history of the ingestible, either prior or contemporaneous with use. Various solid or liquid ingestible compositions are provided for determining storage temperature, temperature of the user, temperature of the ingestible, particularly comestibles, and the like. Of particular interest are polydiacetylene polymers which may be formulated to provide compositions having transition temperature over a broad temperature range.

9 Claims, No Drawings

INGESTIBLES POSSESSING INTRINSIC COLOR CHANGE

This is a divisional of application Ser. No. 09/602,001, filed Jun. 23, 2000, now U.S. Pat. No. 6,607,744.

INTRODUCTION

1. Technical Field

The field of this invention is ingestibles having informative characteristics.

2. Background

Foods, beverages, medications and a variety of edible products with intrinsic color change properties can find a multitude of uses for manufacturers and consumers alike. They can be developed and marketed for entertainment purposes, such as graphics on the surface of food, which change color giving rise to a visual effect that is both pleasing and interesting for children. A variety of new food categories can be produced to contain the chromic material. Food producers are in need of new means to differentiate brands, extend product lines, advertise and promote, and create new product lines. Generally, food developers are limited to new flavors, colors, presentations, packaging, and combinations for product differentiation. Entirely new categories of foods, beverages, and medications can be created by introducing a new intrinsic property during processing.

Color changes may release or expose hidden messages which can be used for promotional or marketing purposes. Color changes can visually signal the consumer when the food is "done" just right and safe to eat or that the food is still in the process of being cooked. Color changes can be used to communicate optically with a cooking instrument telling the cooking instrument the level of doneness through a bar code change.

Color change foods can indicate to consumers or institutions that the food offered is sterile due to its color at purchase. Subsequent changes in color could indicate that the food has become stale. Safe food storage temperatures can be indicated by the food or beverage directly where a color change indicates that the food was held at an inappropriate temperature for a period of time. The color change can be used to signal the timely release of a certain nutrient or flavor into the food. The chromic change can also be used to communicate the nature of food to be consumed. For example, chromic change agents can tell the consumer how "hot" a hot sauce really is, the fat content of certain foods, the level of carbonation in soft drinks, or the level of a biological or chemical in a food, such as caffeine or allergens.

Certain spices and other foods should be irradiated with high energy sources to ensure that potential bacterial contamination has been eliminated, thereby protecting the consumer. Foods containing a chromic agent which indicates a color change upon irradiation can communicate to the consumer or the food processor that proper irradiation has taken place.

Prior Art

Prior art of interest includes U.S. Pat. Nos. 4,859,538; 5,144,112; 5,156,810; 5,189,281; 5,273,360; 5,415,999; 5,685,641; 5,788,375; 5,918,981; and 6,046,455.

SUMMARY OF THE INVENTION

Environmentally responsive components are intrinsically associated with ingestibles, such as foods, beverages and medications, to be consumed as part of the ingestible, while providing knowledge of an informative or entertaining character. Specifically, physiologically acceptable chromic materials, e.g. polymerized polyacetylenes are associated with the ingestible, so as to be consumed by the user. The chromic material changes color in response to various environmental clues, such as temperature, pH, radiation, physical stress, etc.

DESCRIPTION OF THE SPECIFIC EMBODIMENTS

Ingestibles are provided comprising a chromic material, which changes color in response to environmental cues. The color indicating material can be processed directly into the ingestible, coated on the surface, released in a timely manner, or be made to be exposed through a discrete color change triggering process. The chromic materials are physiologically acceptable, particularly polymerized polyacetylenes, which can be incorporated with the ingestible during or after processing. Only a small amount of the chromic material need be incorporated, where the chromic material may be suffused through the ingestible, partially penetrate the ingestible or primarily be an adherent coating on the ingestible. The ingestible is porous or liquid, so that the chromic composition, by itself or in conjunction with an edible carrier, interpenetrates the ingestible, where the penetration may be throughout the ingestible, a limited depth into the ingestible, or into the surface to provide an adherent surface.

A variety of color change triggering processes can be employed to cause the color change depending on the type of chemistry involved, such as temperature, pH changes, changes in ionic strength, mechanical changes such as stress or pressure during mixing or contortion, chemical changes such as the addition of a second component, exposure to light for a photochromic effect, biochemical reactions such as binding pair interaction, solvent environment changes, hydration or dehydration, solvent changes, and enzymatic changes where enzymes in the food can induce a change.

Diacetylenic and polydiacetylenic compounds can be produced in a multitude of forms or substituents for compatibility and functionality with foods, beverages and medications. The diacetylenic group can be modified with lipid-like groups for solid phase or liquid phase compatibility, carbohydrates, sugars, polar and apolar groups, functional groups such as amines, carboxylic acids, alcoholic groups, esters, amides, charge complexes, aliphatic groups, ethers, polyethers, amino acids, proteins, nucleic acids, mesogenic side chains, sulfhydryl groups, block co-polymers and other groups which can be used to create specifically desired characteristics. Compositions can be prepared having up to about 20 weight % of the polydiacetylenic polymer for coating, which compositions further comprise carbohydrates, lipids or other physiologically acceptable composition.

By ingestibles is intended compositions that are taken orally, even though they may not be digested. Therefore, ingestibles include foods, medicaments, toothpaste, mouth washes, gargles, swabs, and the like, where the food is introduced into the mouth and may then be rejected or may reside in the mouth for a limited period of time. Since foods are the primary application of the subject invention, foods will be discussed as illustrative of ingestibles generally.

The diacetylenic compounds or chromic agents present, whether monomers or polymers, in the composition added to the ingestible will generally be present in at least 1 weight %, more usually at least about 5 weight %, and may be 75 weight % or more, usually being not more than about 60 weight %.

Monomer chemistries: Classes of photochromic, thermochromic, hydrochromic, lipochromic, and physiochromic polymers can be made from a variety of organic diacetylenic monomers including short chain molecules with no side chains or substituents, short chain molecules containing one or more functional groups and aliphatic monomers that vary in length from 10 carbon units to 50 or more carbon units with or without various functional side chains or substituents. Molecules can be hydrophobic or hydrophilic depending on the desired application. They can be neutral or charged in order to create a desired intermolecular or intramolecular effect. The molecule can be non-polar, mono-polar, or multi-polar. Diacetylenic monomers can be symmetric or asymmetric. For food grade applications, the monomer and subsequent polymer molecules can contain food compatible groups including sugars, lipid chains, carbohydrate moieties, amino acids, peptides, proteins, complex proteins, effector groups, esters, alcoholic groups, amides, carboxamides, dextrans, heterocyclic substituents, acids, lipids, detachable nutrient groups, such as vitamins and nutraceuticals, catalytic groups such as enzymes, chelating groups, nucleotides, food colors, emulsifier groups, or the like.

Side chains and substituents can be chemically modified for use with a variety of different foods. The hydrophobic or hydrophilic nature of the chemical compound can be adjusted to create compositions more or less compatible with fatty foods, carbohydrate based foods, meats, dry foods, cereals, baked goods or the like.

The diacetylenic monomer will be a lipid mono- or dicarboxylic non-oxo carbonyl monomer or derivative thereof, so that acid, esters, or amides may be employed, a mono- or diol, ether or ester thereof, where the acid may be organic or inorganic, e.g. phosphate, an amino or derivative thereof, where the derivative may be an organic substituent, such as an acyl group, an aliphatic group, an aromatic group, a heterocyclic group, etc. The substituents at the termini will have from 0 to 30, more usually 0 to 20 atoms, which will usually be carbon, oxygen, nitrogen, sulfur and phosphorous. The acid portion of the molecule (or underivatized portion) will generally range from 5–30, more usually 12–30, carbon atoms and the diacetylene groups which will be in conjugation, may be situated symmetrically or asymmetrically in the molecule. Thus, the flanking alkylene groups may be the same or different in a molecule, where the temperature transition of the polymer will depend upon the chain length of the monomer, whether the diacetylene groups are symmetrical or asymmetrical, and the degree of difference between the length of the flanking regions, whether one uses a single monomer to form a homopolymer or two or more monomers, usually not more than four monomers, to form a co-polymer, and whether the chains are substituted or unsubstituted, as well as the nature and degree of substitution. Particularly, halogen substituents, e.g. fluorine, chlorine and bromine, may be present to enhance the upper temperature limits possible with the subject compositions, ranging from a single substituent to persubstituted. The temperature range which is attainable using the various diacetylene monomers will range from about 25–300° C., usually not exceeding 200° C., more usually from about 25–200° C. For the purposes of this invention, the range of interest will be from about 30–200° C., more usually from about 35–200° C., and particularly from about 35–150° C.

For the most part, the diacetylene monomers will have the following formula:

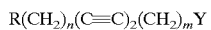

$R(CH_2)_n(C{\equiv}C)_2(CH_2)_mY$ wherein:

Y is $COX^1$, amino (including substituted amino, e.g. alkyl substituted amino of from about 1–6 carbon atoms), oxy having from 0 to 6 carbon atoms, thio of from 0 to 6 carbon atoms, cyano, halo, etc.;

m and n are at least 1 and total 8–25, preferably n is at least 2, more preferably both m and n are at least 2;

R is H or Y; and

X and $X^1$ may be the same or different, usually the same, may be any of the groups indicated above, generally being H, OH, TO, where T is of from 1–8, usually 1–6 carbon atoms having from 0-(n-2) substituents, wherein n is the number of carbon atoms and the substituent may be oxy, amino, halo, thiol, etc, usually aliphatic, e.g. hydroxyalkyl, and aminoalkyl; or $NT^1$, $T^2$, wherein $T^1$ and $T^2$ are the same or different, usually the same and will have from 1–8, usually 1–6 carbon atoms, the total number of carbon atoms of $T^1$ and $T^2$ usually not being greater than about 6 and each having from 0-(n-2) substituents as described above, particularly oxy, one of $T^1$ and $T^2$ may be unsubstituted or substituted amino (hydrazino), where the substituents will come within the definition of $T^1$, polyalkyleneoxy, wherein alkylene is of from 2 to 3 carbon atoms and may have from 2 to 50 units;

or two Y's may be taken together to form a divalent linking group of from about 2 to 2,000 daltons, which will usually be 2 T's taken together (T's include T and $T^1$). Monomers can be used in individually and in pure form. The position of the acetylenic groups may be symmetrical or asymmetrical in the molecule.

Of particular interest are monomers, such as 10,12-tricosadiynoic acid (C23) or 10,12-pentacosadiynoic acid (C25), which can be used independently during processing and production to achieve a lower sensitivity to UV irradiation (254 nm) or either compound may be added in a percentage to the other to sensitize the mixture to make the mixture far more sensitive to UV irradiation. 0.01–50% by weight of C25 can be added to C23 to make a mixture which polymerizes 50% or more quickly and achieves a much darker blue appearance after polymerization. More usually, 0.1 to 30% C25 is added to C23. Typically, 1 to 20% C25 is added to C23. Formulation variations along with UV irradiation times can be used to create different thermochromic temperature settings. Combinations of formulations can be used to achieve a variety of visual effects upon temperature triggering including patterns, which appear to change non-uniformly to create visual imagery such as the appearance of movement in a stationary picture.

The compounds used to react with the carboxyl groups may be selected in relation to the ingestible to be modified. Thus, the groups may be chosen to make the polyacetylenes more compatible with the ingestible, using polar compounds to enhance compatibility with polar ingestibles, non-polar compounds to make the polyacetylenes more compatible with lipid compounds, solubilizing groups which provide for solubility or dispersibility, and the like. Certain photochromic materials can undergo a second color transition upon high heat (greater than 200° F.) from a red color to a yellow color and then reverse colors upon cooling back to room temperature. Among such materials are the dual chain glutamate diacetylene containing lipids, mono-amide glutamate lipids and tri-amide glutamate lipids, can be used alone or in combination to achieve similar effects at lower temperatures. For example, the molecule can be modified to have strong hydrogen bonding characteristics that cause strong intermolecular interactions between monomers along a polymer chain and exerting a strong ordering characteristic along the chain. Strong intramolecular or interpolymer chain hydrogen bonding helps to stiffen and order the polymer backbone. Heading or perturbing the back bone cause a stochastic conformational change along the polymer that results in a color change from a highly ordered blue structure to a red disordered structure. Cooling or reversing conditions allows the intermolecular or intra-polymer chain hydrogen bonding interactions to dominate and re-order the polymer chain to an ordered blue structure. Among such materials are single chain lipids containing one or more amides for promoting intermolecular hydrogen bonding. For example, acetylated ethylene diamide-10,12-triconsdiyneoic amide contains two internal amide linkages along a single chain compound. Alternatively, dual chain lipids containing a mono-, di- or triamide glutamate head group can be used. In addition carboxylic acid lipids where the diacetylenic back bone is in close proximity with the head group (1–4 carbon atoms removed) have a large influence over the polymer structure and can exhibit reversibility (e.g. 4,6-heptadecadiynoic acid) at moderate temperatures (68° F. to 130° F.). Reversible thermochromic materials can made using glutamic acid with two chains of 10,12-tricosadiynoic acid to form a dual chain glutamate lipid. Dual chain glutamate lipids exhibit a high degree of thermochromic reversibility due the interlocking nature of the microcrystalline structure and or their hydrogen bonding characteristics. Generally there will be from 1 to 10, more usually from about 1 to 8 hydrogen forming groups in a repeating unit of the polymer, such as amide, hydroxy, keto, amino, etc.

Reversible color changes are important for ingestible applications where the ingestible undergoes a temperature change from one level to another level and then back to the original temperature level and it is desirable to use the color changes between temperature levels to communicate to the observer characteristics about the ingestible. For example, a reversible color change can be used on a cereal where at room temperature the cereal is red. Upon addition of milk, the cereal will be cooled by the addition of cold milk causing the polymer to become blue.

Irreversible color changes in polydiacetylenes can be introduced by eliminating or reducing the inermolecular or intra-polymer chain hydrogen bonding characteristics. For example, the polydiacetylenic moecule can be apure hydrocarbon structure without substituents, an ester or have other relatively non-interactive groups.

Irreversible color changes are important to ingestibles containing them when it is desired to observe a color change at a certain temperature level and it is desired to maintain "memory" of the temperature level achieved at a given time or location. It is convenient to use irreversible thermochromic color change in polydiacetylenes during a temperature increase converting the blue form of the color to a red form. For example, a thermochromic message can be revealed on a toaster pastry and the message is permanent until the pastry is ingested.

Likewise, the substituents can be added to provide for other means to disrupt or order the polymer structure and thereby cause a reversible or irreversible color change in the polymer backbone. For example, mono- or multiple alcoholic groups can be introduced to promote interaction with hydrating or solvating solutions. Solvent or hydrochromic color changes are particularly attractive when combining dry ingestibles with wet or moist ingestibles. For example, adding milk to cold cereal, dipping cookies or crackers in milk, adding crackers to soup, pouring liquid syrups on breads or pancakes, adding salad dressings to salads, or the like, can be the trigger for a color change.

In addition, solvent/hydrochromic effects can be used in unique ways to propagate a color change along a surface. As hydration occurs along an absorbent layer and themoisture migrates, a blue form of the polymer sensitive to solvation or hydration will turn the disordered red from of the polymer to the ordered blue form. Messages or graphic can be visualized sequentially to create time resolved graphic changes.

pH sensitive groups, e.g. bases and acids, such as a hydrazide or a free amine group can be attached to the head group of a lipid or hydrocarbon moiety to invoke a pH triggering response to the blue form of the polydiacetylenic polymer to a red form of the polydiacetylenic polymer. Ethylene glycol or polyethylene glycol groups can be attached to the monomeric material to alter the solubility with different food types or help to emulsify the monomeric chromic agent.

Ethylene glycol linkers can range from a single ethylene oxide unit to 50 units. More typically they may range from 2 to 20 units and most conveniently from 3 to 6 units. The number of units can be changed depending on the desired level of hydrophobic or hydrophilic nature for the resulting molecule.

Depending on the type of application, it may be desirable to have an irreversible thermochromic or physiochromic event or a reversible event. Hot liquids containing a reversible thermochromic for example can be made to turn red at a high temperature and back to blue at some intermediate or room temperature. Upon reheating, the liquid would turn red again. Cereals containing a low temperature reversible chromic material can be red at room temperature and change to blue upon addition of cold milk. An irreversible thermochromic can be used to show a pattern change in a solid pastry indicating that the pastry was indeed heated to a certain temperature to reveal a message or picture which stays the same even after cooling. Single chain monomers such as 10,12-tricosadiynoic acid can polymerized to form an irreversible thermochromic property.

For lower temperature applications such as visualizing a color change when a food is brought to room temperature or above, it is desirable to have a thermochromic compound which responds immediately to an ambient room temperature. 10,12-tricosadiynoic acid or 10,12-pentacosadiynoic acid can be converted to the methyl ester form to create materials, which change color form, a deep dark blue to irreversible bright red, at about 80° F. These can be useful for indicating that certain foods, which should be stored at less than room temperature, have been raised or heated to higher than room temperature. For example, in some cases like certain medications, dairy products or foods, it is desirable store them at room temperature or below and keep them from being raised even slightly above room temperature. In these cases, it may be desirable to incorporate a thermochromic material, which tells consumers that the product has at one time been held at an undesirable high temperature and should no longer be consumed. In these case it is highly advantageous to have the thermochromic material in direct contact with the consumable medication or food and not with packaging so that no false indications are made and expensive items are not inappropriately thrown out. Shorter hydrocarbon chains attached to the diacetylenic backbone can also be incorporated to reduce the energy or impact required to trigger a chromic transition. A balance between the hydrogen bonding, Van der Waals interactions, charge-charge interactions, hydrophobic-hydrophilic interactions, can be achieved to produce the desired type and situation for color changing ingestibles.

Hydrogen bonding functional groups attached to monomers can be used to influence the chromic properties of corresponding polymers. Tightly hydrogen-bonding groups can increase the energy required for the chromic material to change color. Reducing the hydrogen bonding capabilities of the chromic material can be used to reduce the energy or degree of change in environment to cause a color change. Hydrogen-bonding groups include polar atoms, such as oxygen and nitrogen, to which the hydrogen is bound. Hydrogen bonding can be structured between individual chromic molecules or between chromic molecules and surrounding carrier materials with which they are in association.

Formulations and compositions: Monomeric or polymeric chromic change materials can be combined with a carrier material to form a composition which makes it possible to be applied to and/or adhered to foods. Carrier materials can range from a simple aqueous solution to complex mixtures containing different emulsifiers, flavors, or foodstuff. Constituents such as oils, lipids, sugars, salts, lectins, agglutinins, protein matrices, carbohydrate matrices or the like can be combined alone or together with an unpolymerized agent or polymerized agent to give the agent the properties necessary for transfer to, adherence with, or stability on a food type.

Carrier materials suitable for printing can include aqueous solutions or pastes, which are applied and dried more slowly. Alternatively, the solution can contain an ethanol base, which can be dried more quickly. The carrier for printing can contain any food compatible composition.

Carrier materials suitable for extrusion can contain thickening substances to give it the consistency for rapid extrusion and pattern formation on the food surface of interest. Starches, methylcellulose, but pastes, dextrins, polydextrins, protein pastes, sugars, dried gelatins, rice papers, doughs, frostings, sugar-based papers, edible inks, edible waxes, ingestible polymer substrates, caramelized sugars, or the like can be used for a support surface to which the chromic agent can be applied. Thickened carriers provide for the ability for form three dimensional structures such as overlaying lines or patterns which can enhance the contrast for the thermochromic or physiochromic color transition. Carriers suitable for lamination can include substances which provide for stable layers to be applied to the food of interest.

Binding agents can be used to integrate more or less of the chromic material with a particular food type. In most cases it is desirable to tightly bind the chromic material to the food so that the material stays visibly in contact with the particular part of the food portion it is initially on and that the material does not slough off into a surrounding liquid or rub off on any packaging materials. Binding agents can include sugars, carbohydrates, proteins, methyl cellulose, and other materials commonly used to bind food colors, coatings, frostings, sprinkles and the like. The binding agent can be co-mixed with the chromic material, coated after application of the chromic material to form a protective layer or used in combination with both the food and the chromic material.

Various traditional inactive ingredients can be used to co-mix, pre-color or adhere the chromic agent to a support surface on the consumable product including: hydroxypropyl cellulose, hydroxypropyl methyl cellulose, microcrystalline cellulose, starch, red iron oxide, magnesium stearate, titanium dioxide, talc, colloidal silicon dioxide, polyethylene glycol, various synthetic polymers, Yellow 10 dye, carnauba wax, corn starch, sodium starch glucolate, or the like. These various additives are conventional and will be present, when employed, in a range of from about 0.1 to 95 weight %.

Configurations of application for chewable foods: The chromic material, such as diacetylenes, need to be in a microcrystalline phase in order to polymerize to the chromic material. Therefore, if the diacetylenes are to be mixed with other components that adversely affect the formation of the microcrystalline phase, the diacetylenes will normally be prepolymerized before formulation. Solution phase chromic material or monomer can be applied to a chewable food surface, dried and then polymerized. Liquid phase monomer can be polymerized if in a colloidal/crystalline form, applied to a solid food surface and dried. Solid microcrystalline monomer can be admixed with food carriers, applied to a solid food surface and then polymerized. Solid microcrystalline monomer can be first admixed with a food carrier, polymerized and then applied to a food surface. Solid microcrystalline monomer can be first polymerized, admixed with a food carrier and then applied to a food surface.

The solid surface of the food may be processed to accept the monomer or chromic material. In many cases, if the food surface is too porous, the monomer or chromic material will dissipate into the interstitial spaces below the surface rendering it unavailable for visualization. Solid food surfaces can be prepared for accepting the monomer or chromic material by modification of the food composition or coating the surface with a composition, which seals the food surface. In either case, application of the monomer or chromic material to the food surface will provide for a means to keep the material on the surface and visible. Illustrative of such situations are sugars, proteins, digestible celluloses, methylcellulose, polydextrins, digestible waxes and gums, which can also be used to create a smooth hydrophobic barrier for even coating of the physiochromic agent.

Structures containing the physiochromic agent can be created which come in contact with the food type of interest. The structures themselves can be compatible with food and can be made with digestible components or can be made of material which is certified for contact with food but not meant for consumption. Structures can be labels, part of the package, an insert in the package, paper rings, tabs or the like. The structures can be printed with the physiochromic material in a way in which the structure can interact with the food. For example, the structure can be an adherent label containing a thermochromic form of the agent. The adherent label can be adhered to a food type meant for heating. When the food is heated, the thermochromic agent will change color. If the label structure is edible, it can remain in contact with the food type and be consumed along with the food. If the structure is safe for food contact but not edible, then it can be removed prior to consumption.

The monomeric or polymeric form of the chromic agent can be fused or admixed into foods or medications. For example, a polymerized liposomal or colloidal form of polydiacetylenic material can be processed with gelatin to produce a thermochromic form of desert gelatin. At refrigerator temperatures (40° F.), the gelatin could appear dark blue. When raised to room temperature (68° F.), the gelatin would turn bright red/orange. Alternatively, a polymeric chromic agent could be cast into a throat lozenge. A chromic agent which undergoes a temperature transition from dark blue to red/orange at 100° F. could be employed to help a consumer determine if they have a fever. Usage of the lozenge would indicate to the consumer that they have a low grade fever if the lozenge turns red/orange. The consumer could also examine his tongue to see if either a red or a blue color has come off the lozenge. Blue would indicate no fever and red/orange would indicate a low-grade fever.

The thermochromic material can be patterned alone or in combination with food-based inks to create bar codes. Bar codes can be utilized in connection with cooking where the cooking system, equipped with a bar code scanner, can measure a change in the bar code as the code is exposed to high temperatures. Bars on the code can be made to change color when one or more temperatures are achieved. The optical density change in a given bar will result in a prescribed change and interpreted by the measuring system to indicate a specific temperature. The bar code can indicate doneness or in process cooking. The bar code can be printed directly on the solid food type. This allows the bar code and bar code reader to be used as a temperature measure device.

Configurations of application for liquids: Liquid phase monomer can be included in an unpolymerized form in a beverage or consumable fluid, such as a syrup where the monomer is in a colloidal or microcrystalline state. The monomer can be directly polymerized with a UV light source or sun light. The solution suspension monomer can also be pre-polymerized and then added to a liquid phase consumable. The monomer can be made water-soluble using short chain compounds, which are mono- or bi-polar. In this case, the monomer must be prepolymerized in a solid form and then solubilized after polymerization. Polydiacetylenes undergo a topochemical polymerization and must be in a crystalline state in order for polymerization to occur. Monomeric lipophilic forms of diacetylenic compounds can form colloidal particles, such as liposomes, vesicles, or other lamellular forms. Lipophilic forms of the monomer can be crystallized in a colloidal state and polymerized while the monomer is suspended in an aqueous solution. Colloidial or microcrystalline suspensions of monomeric diacetylene can be made using ultrasonication or standard reverse phase vesicle formation methods. Heating and cooling cycles along with intense sonicationcan be useful for improving uniformity and homogeneity of the suspensions.

For alcoholic beverages, the monomer can be processed into the beverages using reverse phase vesicle formation. The monomer can be dissolved in ethanol and combined with the beverage aqueous constituents. Vesicle formation can be accomplished using standard processes. After the beverage has been formulated, polymerization of the monomer can be accomplished using standard polymerization methods.

Methods for application to foods: Compositions containing either pre-polymerized material or monomer material can be processed into foods using a variety of application methods such as ink jet printing, pad printing, extrusion, spraying, liquid applicators, dip coating, sublimation, spreading, application of laminates containing the material such as sugar layers or rice paper, edible labels, dripping, dye sublimation printing or the like. The method of interest will depend on the food substrate utilized, the composition to be applied and the desired format, in which the composition is to be placed.

For application to cereals, it is desirable to place the photochromic, thermochromic, or physiochromic material in a carrier material such as a sugar matrix whereby the matrix is applied as a coating to the cereal during production. For application to convenience foods such as flat pastries or cookies where patterning is important, high speed printing techniques are important. In this case it is desirable to use a soluble form of the material so that it can be incorporated directly into the liquid matrix used for printing.

The monomer or polymeric material can be applied to a solid food using a laminate overlay where the base material in the overlay/laminate is itself edible and contains the monomeric or polymeric color change material. Rice paper can be used as a laminating material which when wetted and containing the polymer can be easily adhered to the food as a substrate. Laminates can contain the chromic agent in combination with sugars, carbohydrates, digestible polysugars, or proteins, which give the laminate a stable layer. The layer can have the property of being directly layered on to a food surface, fused and then activated for photochromic, thermochromic or physiochromic activity. Food laminates capable of containing the chromic material can be any commercially available product or formulation that is physiologically acceptable and can be printed or coated. For example, the laminate can be a marzipan sheet available through most bakery supply sources. The thin sheet can be printed, stamped, blotted with the chromic material by any convenient means, dried and polymerized. The laminate can then be adhered to the food type surface alone or with food pastes.

Commercially available laminate/paper materials compatible with ink jet printing can be used (Kopykake, Torrance, Calif.). Commercially available ink jets can be modified to contain an ink version of the chromic agent. The ink jet cartridge can be used with an aqueous or solvent-based solution containing the chromic agent. The food grade laminate/paper can be inserted into the ink jet printer and standard ink graphics printing programs utilized to generate text and graphics. The laminate approach provides a means for generating high-resolution graphics and text and transferring the images or text directly to the food type. The laminate can be made to be compatible with the food flavor and texture. For example, it is desirable to have a sugar based laminate for sweet products such as pastries, cookies, and certain convenience foods. Alternatively, it is desirable to have a salt/seasoning-flavored laminate for dairy or processed meat products. The exact composition, flavor, and texture of the laminate will depend on the food component into which the chromic material is integrated. Laminates have the advantage of being separately prepared from the food product and then processed to be a part of the food. Parallel processing provides for high-speed production and simplified implementation.

Edible food grade labels, paper or wrappers containing the chromic material can be used for a wide range of general applications. The label can be made with a digestible carbohydrate material rather than a non-digestible cellulosic material. Printing the chromic material can be accomplished by standard printing means. The printed chromic label can be applied to any solid and reasonably flat surface such as a cookie, a toaster pastry, baked goods, and a variety of convenience foods. A major advantage to chromic labels is that they can be pre-mass produced and subsequently applied to finished foods rather than requiring changes in existing food production processes. The chromic material can made soluble in ethanol or various highly volatile solvents, which can be quickly evaporated, or in an aqueous solution, which can be absorbed. In any case, it is desirable to coat the surface of the food substrate with the chromic material so that upon polymerization the chromic material is highly visible. The substrate can be dipped into a solution containing the chromic agent thereby coating the agent on the substrate's surface.

Entertainment foods such as marshmallows can incorporate the chromic material using dip coating or spraying processes to provide an extra level of enjoyment to children.

Chromic marshmallows can be produced to respond to ambient temperatures such as touch or elevated temperature fluids, like hot chocolate. Marshmallows can be directly dip coated with a higher temperature thermochromic material dissolved in an alcoholic solution. After drying and polymerization to produce the dark colored chromic agent, the marshmallows would remain dark until exposure to high temperatures such as an open flame. Upon exposure to any elevated temperature, the dark marshmallow would turn bright orange-red.

Alternative means of incorporating the chromic agent into foods could include biochemical substitution. Fruits, vegetables, certain meats, bacterial cultured dairy products such as yogurt, grains, rice, beans or other amenable foods can be grown with the precursor monomeric material as a nutrient for the growing food. Upon incorporation or biochemical uptake of the precursor monomer through the appropriate pathway into the food product, the food can be irradiated with UV 254 nm to cause polymerization of the food stuff. Various dairy products such as cheeses, milks, and yogurts which naturally contain bacterial cultures to aid in digestion can be made with monomeric and/or polymeric chromic agents.

Methods for polymerization: Polymerization can be accomplished either prior to processing with the food or after the monomer has been processed with the food. The photochromic properties of the chromic material can be used to create patterns and messages on the surface of solid foods. Increasing or decreasing the level of polymerization of the chromic material is used to correspondingly increase or decrease the temperature or other means of inducing color changes in the polymer—food matrix or the like used to trigger a chromic change in the material. For example, different zones of a food surface, which contains the chromic material, can be polymerized to different levels. Each zone can, depending on the level of polymerization exposure, change color sequentially as the temperature rises. The chromic change zones can tell consumers that cooking is in progress but not yet done. As cooking continues, and as the last zone changes color the consumer can tell that cooking is complete. Zones which change colors at increasing temperature can be used for food safety purposes indicating to consumers when the food is cooked to a temperature level which indicates any contaminating bacteria have been killed (e.g. 160° F.). Zones would be calibrated to accommodate higher external temperatures during cooking.

Increasing or decreasing the localized concentration of chromic material in combination with controlling the local level of polymerization can be used to create complex patterns on the surface of a food type. Increasing the local concentration in one area relative to another area will create a higher relative triggering temperature in the high concentration zone relative to the lower concentration zone. The patterns can be developed to create the visual appearance of a changing graphic through out the temperature triggering process.

In addition, standard food colors can be used in combination with the chromic material to create full color designs and patterns. The visual representation of a graphic which changes color and apparent pattern throughout the heating process can have significant value in that it can be used for commercial, promotional, merchandising and advertisement purposes. In some cases, polymerization can be accomplished by the consumer where by opening a package and placing the food stuff in the sun light, a color begins to appear immediately prior to consumption. For example, drinks or cookies can be made to change color in the sun. In other product formats, the photochromic food may be purchased along with an appliance or hand held UV lamp which can be use to expose the photochromic material.

Thermal polymerization can be utilized in certain foods. Thermal polymerization provides for photochromic color development of the chromic agent without the need for an external UV light source. Certain forms of diacetylenic compounds, which are highly ordered yet, provide flexibility for reorganization can self initiate polymerization under mild conditions. For example, the crystalline form of the methylester of 10,12-tricosadiynoic acid will polymerize in the dark and in absence of UV light. The thermal polymerization temperature may be substantially different from the thermal color change transition temperature. Polymerization may occur at a lower temperature, e.g. 10–20° F., than the thermal transition temperature.

Patterns in the chromic agent can be generated by selectively placing the agent in locations using methods such as ink jet, pad, extrusion or off-set printing followed by polymerization of the chromic agent. Alternatively, the patterns can be generated using a continuous evenly coated area of the chromic agent followed by photo-masking techniques. Ultraviolet light transmitting photo-masks can be utilized. In either case, high resolution graphics and line art can be generated directly on the food surface.

Methods for triggering color change: The chromic change can be tailored to match a desired effect or outcome in a particular food or ingestible. Color change triggering process can include temperature, pH changes, changes in ionic strength, mechanical changes such as stress or pressure during mixing or contortion, chemical changes such as the addition of a second component, exposure to light for a photochromic effect, biochemical reactions such as binding pair interaction, solvent environment changes, hydration or dehydration, solvent changes, and enzymatic changes where enzymes in the food can induce a change. pH, temperature and other physiologic changes can be induced by finger touch or contact with saliva. Saliva is relatively acidic and can be used to induce an acidic environment which can cause a chromic change in foods containing the chromic material. For example, the chromic material can be sensitized to respond to physiologic temperatures (98° F.). The methyl or ethyl ester of 10,12-tricosadiynoic acid or 10,12-pentacosadiynoic acid is made by standard esterification in methanol or ethanol respectively. The ester compound can be applied to foodstuffs, crystallized and then polymerized at or below room temperature. The dark chromic material is extremely sensitive to thermal contact and changes color immediately at 70° F. for the tricosadiynoate ester and at 80° F. or above for the pentacosadiynoate ester.

Physiologic changes in pH, ionic strength, or hydrogen bonding agents can be used to alter the state of the chromic material. Physiochromic agents are color changing agents that change color in response to a physiologic parameter, such as pH or temperature. Physiochromic matrices can be formulated to hold the chromic agent in one state until the matrix is dissolved. Once the matrix is dissolved and its effect on holding the chromic agent in one state, the chromic agent is free to change conformation to another state. For example, an acid sensitive pH reversible physiochromic agent can be dried down with an acid. The acidity can hold the polymer in one colored state. The local concentration of acid is high in the dry state. When a physiologic buffered solution is added, the acid is released and neutralized by the buffer. The physiochromic agent can now covert to an alternative color since it is bathed in a basic environment.

Combination colors can be integrated along with the chromic material to create a variety of color change effects.

For example, the brown color used in a variety of food types is made with a combination of yellow, red and blue. The blue food color can be replaced with a blue form of the chromic agent. Upon color change triggering, the brown food color combination can be converted to a bright red-orange. Examples of brown colored foods or beverages include brownie mixes, hot and cold chocolate drinks, cinnamon colors, and the like.

The physical, conformational, or polymerization state change can be used as a mechanism to release or change certain embedded flavors, nutrients, aromatic compounds, nutraceutical agents or the like. For example, a flavor material can be chemically coupled to a monomer non-chromic form compound. In the monomeric form the compound-flavoring expresses a flavor whereas upon polymerization, the monomer becomes polymerized consequently restricting the flavoring to interact with taste receptors. The restricted form of the flavoring becomes non-flavored. The release mechanism is simultaneously traced with a physiochromic color change as an indicator.

Alternatively, conformational changes in the chromic material matrix can be utilized to release various food grade compounds. For example polydiacetylene in its blue form is highly ordered on the molecular level. During processing and polymerization, a food grade compound such as a vitamin or flavor can be trapped. Upon temperature or physiochromic triggering of the polydiacetylenic material to the red form, the polydiacetylene becomes disordered and opens at various positions. During the conformational disordering of the polymer, the vitamin or flavor can be released. The monomeric form of the chromic material can be used to absorb and allow in the flavor or aroma. Polymerization could be used to trap in the flavor or aroma. The ordered blue form of the polymer may hold a flavor or aroma where heating results in a conformational change and disorder in the polymer which is useful to release the flavor or aroma.

Specific physiochromic changes may be desirable when developing foods which a producer would like to differentiate from a competitors. Binding moieties can be used to facilitate specific photochromic, thermochromic, or physiochromic color transitions. Lectin-receptor agglutinin-receptor, antibody-antigen, biotin-avidin interactions or the like can be used to stimulate a binding pair interaction between different food components. Binding pair interactions can be used to create specific calorimeter changes in the chromic agent. For example, a combination of milk and cereal can be formulated in which a specific type of milk contains one member if a binding pair, such as a multiple biotinylated milk protein and the cereal contains a biologically active form of the physiochromic agent that contains avidin or streptavidin as a second member of the binding pair. When the specific milk comes in contact with the specific cereal, then only that milk will cause the specific cereal to change color through the binding interactions of the binding pair members. No other milk or cereal combinations could cause a chromic change without the selective interactions of those binding pair members. This scenario can help food manufacturers create novel means of brand differentiation.

Carbonation pressure release in opening sealed carbonated beverages may be used to induce a local stress/concentration change, which could cause a color triggering changes in the chromic material. For example, the inside of a liquid container can be coated with a pH or friction sensitive version of the physiochromic material. Upon opening the container and release of built up pressure to ambient conditions, the process of bubble nucleation and local carbonic acid concentration change may be used to cause a change from environmental condition/conformation of the color change agent to another form of the material. If the container is clear, the color change can be made evident to the observer of the color change. The color change agent can either be in a water solution form such as contained within a liposome structure or be coated on the inner wall of the container.

For hydration activated color change, physiochromic agents which change color depending on the degree of salvation or hydration can be used (hydrochromic agents). Color change agents capable of changing color upon partial or complete hydration and can be ingestible can find multiple uses for food or food related products. For example, the bi-polar diacetylenic compound 4,6-decadiynek-1,10-diol when adhered to a surface and polymerized at room temperature forms a deep blue/purple polymer. The blue/purple polymeric form of the material changes to a red/orange color upon hydration both below or above the melting transition of the material. One mechanism for inducing the color change may be rapid intercalation of water between the layers of the crystalline lattice where the aqueous phase disrupts the ordered polymer lattice.

The hydrochromic agent's rate of color change is temperature and configuration dependent. For example, the rate of color change from the blue/purple color to a red/orange color is rapid and occurs within a minute when a thin layer of the hydrochromic agent is uniformly spread over a dry porous structure and exposed to an aqueous fluid at or 10° F. below the melting transition of the material. The color change is slowed significantly from one to several hours if the hydrochromic agent is applied in a thick layer (0.1 to 1.0 mm) and treated with an aqueous solution near freezing.

The hydrochromic agent can be placed on an ancillary material such as the carbohydrates, granulated sugar, sugar sprinkles, fondant, sugar pastes, candies, etc., nutritional bits, food coatings, condiments, carriers, emulsifiers, coating materials or the like and subsequently applied to the food surface. For example, the diacetylenic compound 4,6-decadiyne-1,10-diol can be conveniently dissolved in an alcoholic solution (0.15 g/ml) and the solution applied to white or colored sugar sprinkles. Upon coating, drying and polymerization, the sugar sprinkles can subsequently be adhered to a cookie, cereal, candy, bread, cake or the like. The dark blue/purple sprinkle changes to an orange/red color immediately upon treatment with water, milk or other liquids capable of disrupting the crystal packing of the chromic agent.

The use of hydrochromic agent pre-coated sugars, salts or other carriers has the advantage of providing a high degree of coloration and surface area for fluid contact. For example, a fine hydrochromic/sugar particle coating creates capillary channels for fluid to wick through thereby facilitating the hydration process.

Other structures may also conveniently contain the hydrochromic agent placing it in close or intimate contact with foods. For example, the material can be placed on a bowl, spoon, plate, fork, straws, a hydrating strip, a package insert, part of the package or the like, such that a portion of an absorbent material can be in liquid contact with an ingestible liquid. As the liquid hydrates the structure, the liquid solvent hydrates and migrates along the structure causing the physiochromic agent to change color. If the structure containing the agent is edible, it can remain in contact with the ingestible liquid and be consumed. If the structure containing the agent is safe for contact with food, but inedible, the structure can be removed prior to consumption of the ingestible liquid.

Mechanical/frictional means can be used to induce color changes in a variety of food compatible products. Color changes can be induced using mechanical means primarily including friction due to rubbing, elasticity, and shearing. For visible friction induced color changes, the color change agent can be permeated into or placed on a surface. Rubbing, stretching, and shearing or other stress causing action can be used to induce a frictional force on the color change agent resulting in localized heating. The ease and magnitude of color change is dependent on the transition temperature of the chromic agent, the friction coefficient between the molecules in the composite or a rubbing tool and the thermal insulative/conductive properties of the composite or rubbing tool. Rubbing tools can include a person's fingers, finger nails, teeth, a wooden stick, a plastic implement or the like. Materials that are more thermally insulative may result in more thermal energy remaining with the chromic agent and less being transferred to the composite or rubbing tool. Metal rubbing tools serve as poor devices for inducing a frictional color change, whereas insulative materials such as plastic or wood provide an easier means for inducing a color change.

Mechanical/frictional color change methods are attractive for revealing messages, altering graphics, introducing codes, creating sweepstakes, creating entertaining graphics or the like. Touching, rubbing mixing, chewing, breading and various other forms of handling can be used to induce the color change. The color change agent must be responsive to the available amount of frictional forces. The agent must also be stable to ambient temperatures and humidity conditions or a color change may result from influences other than frictional/mechanical forces. An exemplary compound, the blue polymeric form of 10,12-octadecadiynoic acid exhibits good thermal stability up to 100° F. with full hydration, whereas rubbing the dry form of the blue polymer easily triggers the polymer to the red form of the polymer.

Mechanical/frictional triggering can be performed directly on a food surface, on a laminate in contact with the food or on a generic surface. In each case, the triggering process can be used to reveal hidden messages, illuminate branding messages, provide a means of interactive graphic changes or the like.

The mechanochromic material can be applied to a surface by a variety of means including application of a solvent containing the chromic agent by means of ink jet printing, spraying off-set printing processes, blotting, pad printing, dipping or soaking. Concentrations of the chromic agent can be from about 2 g/ml to 0.01 g/ml, typically in the range of from about 1 g/ml to 0.05 g/ml, usually from about 0.5 g/ml to 0.1 g/ml. Alternatively, the chromic agent can be applied using transfer methods such as thermal transfer, rubbing from a solid, from a molten liquid or the like.

Photoactivation can be used to cause color changes in foods or food related products when an appropriate photochromic agent is introduced. Convenience foods containing a photochromic agent when placed in sun light provide an entertaining means to create a variety of effects. For example, cookies, cereals and various other convenience foods can be used to reveal various logos, branding identities, codes, sweepstakes information, messages or co-merchandising items to the consumer.

The photochromic agent can be patterned on or applied to the food or implement in contact with the food by means disclosed earlier. Photochromic agents have the advantage of not requiring incidental heat of fluids to create a visual effect. Depending on the photochromic agent, the food can either turn from a natural food color to a new hue or from a given hue to an alternate hue.

For thermochromic agents, temperature ranges can include cold temperature for frozen and then thawing (−20° F. to above 32° F.+), low temperatures from refrigerator levels to room temperature (33° F. to 60° F.), moderate room temperatures to moderately above room temperature and overlapping temperatures from (61° F. to 100° F.), and room temperature to moderate to high cooking temperatures (70° F. up to 200° F.). The final temperature triggering range for the chromic agent is dictated by the hydrocarbon chain length of the molecule, the intermolecular hydrogen bonding capabilities of the molecule's head group, additional side chains of moieties which influence intermolecular attractions or repulsions or the like, environmental effectors which impact the final temperature triggering transition for the chromic agent, and the degree of polymerization which the chromic material is exposed to. Guidelines can be given, but for a particular transition temperature change, the actual change must be determined experimentally. One can try different amounts of the effectors and graph the effect of the concentration of effectors with the change in transition temperature. A curve is produced which allows the determination of the amount of effector, with the change in transition temperature.

Environmental effectors combined with chromic agent to increase or decrease the thermochromic transition of a given thermochromic agent include: various oils, waxes, low levels of organic solvents such as alcohols, ketones, ethers, chloro- and fluorocarbons, metal ions and other ionic compounds, chelating compounds, emulsifiers, or the like. The effector material can change thermochromic transition by altering the energy required to induce a thermochromic transition in the agent. Oils and organic solvents can interact with the long chain hydrocarbons of a C23 or C25 polydiacetylenic acid. The chain packing can be disrupted by the effector to create a metastable state in the polymer that can, in turn, change color at a lower temperature. For example, the temperature transition can be lowered for a polymerized C25 polydiacetylene polymer in its native dry crystalline state from a temperature range of 150° F.–170° F. (depending on the degree of polymerization) down to 120° F.–130° F. by suspending the crystals in a sugar syrup and adding trace amounts of ethanol. Concentrations of oils or solvents added to a matrix can be from 0.001% to 100%, based on 100% of diyine, more usually from 0.01% to 50%, and typically from 0.1% to 10%.

The melting transition of the wax or oil in contact with the chromic agent can directly increase or decrease the intrinsic temperature transition of the chromic agent. Oils that solidify under freezing temperatures can stabilize the chromic agent. Upon a temperature increase above melting transition of the oil or wax, the melting process can facilitate the melting of a hydrocarbon side chain on the chromic agent causing it to undergo a thermochromic transition. The final thermochromic agent triggering temperature can be further adjusted by selecting a specific temperature at which polymerization of the chromic agent is performed. Polymerization at subzero temperatures (−10° F.) lowers the final triggering temperature relative to polymerization at temperatures just above freezing (10° F.). Thermochromic transition temperatures can be increased by increasing intermolecular stability, such as promoting hydrogen bonding of hydrophobic interactions, both between monomeric units within a given thermochromic polymer chain and between the polymer chain and a given effector molecule. For example, the transition triggering temperature of a C23 or C25 polydiacetylenic acid polymer can be increased by embedding the polymer in a high temperature melting paraffin or wax. The thermochromic material can be embedded in waxes from a concentration of 0.01% to 99%. More usually from 0.1% to 50% and typically from 1% to 10%.

EXAMPLES AND EXPERIMENTAL CONDITIONS

Specific foods which have been or can be used with the subject invention as illustrative of food ingestibles generally or other compositions that are taken orally.
Kellogg's Pop-tarts
Nabisco Cream of Wheat
Marshmallows
Kellogg's Rice Crispy Treats
Easy Bake Oven Products
Karo Syrup
Kellogg's Fruit Loops
Kraft Foods Jell-O
Hormel Franks Bologna
Pepperidge Farm Goldfish Soup Crackers
Nabisco Newtons
Flinstone vitamins
Tums antacid
Crest Tooth Paste
Listerine Mouthwash
Throat lozenges
French toast sticks—Burger King Cinnamon Buns—Pillsbury—frosting
Cinnamon Minis—Special dip frosting—Burger King Synthesis of methyl 10,12-pentacosadiynoate (MePDA): 10,12-pentacosadiynoic acid (10 gm, GFS Chemicals) was dissolved in a solution containing 10 ml methanol (HPLC grade) and 10 ml chloroform (HPLC grade). The solution was stirred at room temperature and 10 drops of neat sulfuric acid was added drop wise. The solution was warmed to 100° F. for 2 hour. The reaction mixture was purified using column chromatography. The product (MePDA) was dried using a rotovap and the material stored in a chloroform solution. The solid form of MePDA was very unstable to polymerization and therefore kept dissolved in organic solutions.

Synthesis of methyl 10,12-tricosadiynoate (MeTDA): 10,12-tricosadiynoic acid (10 gm, GFS Chemicals) was dissolved in a solution containing 10 ml methanol (HPLC grade) and 10 ml chloroform (HPLC grade). The solution was stirred at room temperature and 10 drops of neat sulfuric acid was added drop wise. The solution was warmed to 100° F. for 2 hour. The reaction mixture was purified using column chromatography. The product (MeTDA) was dried using a rotovap and the material stored in a chloroform solution. The solid form of MeTDA was very unstable to polymerization and therefore kept dissolved in organic solutions. Alcoholic solutions of MePDA and MeTDA: Solids MePDA or MeTDA were dissolved in reagent grade ethanol to a concentration of 150 mg/ml. An residual polymer was removed by filtration through Whatman No. 1 filter paper. The solutions was held at room temperature or slightly above (70–75° F.) to avoid crystallization or precipitation.

Synthesis of dimethyl bis (10,12-pentacosadiynl oxyethyl) ammonium chloride (BRONCO): 10,12-Pentacosadiynoic acid (5 gm. 13.4 mmol., GFS Chemicals) was dissolved in 60 ml dichloromethane and filtered (Whatman No.1) resulting in a colorless solution. 1,3-Dicyclohexylcarbodiimide (3.6 gm, 17.5 mmol., Aldrich Chemical Corp.) and the base 4-dimethylaminopyridine (one equivalent, Aldrich Chemical Corp.) were added to the solution and stirred for 15–20 minutes during which time a white crystalline precipitate, dicyclohexylurea, formed. Bis (2-hydroxyethyl) dimethylammonium chloride (1.14 gm., 6.68 mmol., Acros Organics—Fisher Scientific) was added to the reaction mixture and stirred over night in a dry inert atmosphere (nitrogen). The urea precipitate was filtered out using (Whatman No. 1) and the reaction mixture was purified using column chromatography. Dimethyl bis (10, 12-pentacosadiynl oxyethyl) ammonium chloride, Bronco, was dried using rotovap and stored in a powder form.

Alcoholic Monomer Solution of TDA/PDA: 10,12-Tricosadiynoic acid (TDA, 6 gm GFS Chemicals) and 10,12-pentacosadiynoic acid (PDA, 0.9 gm GFS Chemicals) were dissolved in 60 ml ethanol (Fisher). The solution was slightly warmed and stirred. The solution (TDA/PDA) was filtered (Whatman No. 1) to remove residual polymer. Dye colorant could be added to the alcoholic monomer solution as an indicator. Standard organic solvent based dyes were added at 2 drops per ml.

Ink Jet Printing: Black ink jet cartridges (Hewlett Packard 680C compatible or Cannon BJC-2000) were modified to contain either the TDA/PDA or MePDA alcoholic monomer solutions. The cartridges were opened and the water based ink removed. The cartridges were flushed with ethanol and the alcoholic monomer solutions added separately to each cartridge. The cartridges were sealed, purged, and inserted into an ink jet printer (Hewlett Packard 680C or Canon BJC-2000). Standard word processing and graphics programs were utilized for printing. The ink jet cartridges were cleaned periodically to remove residual build up of monomer caused by drying.

Ink Jet Printed Thermochromic Sugar Laminates: Edible laminates for ink jet printing (Kopykake, Torrance, Calif.) were printed using the TDA/PDA or MePDA monomer solutions, food grade ink jet dyes, and the ink jet printing systems described above.

Air Brush Coating Surfaces: Alcoholic solutions contain TDA, PDA, TDA/PDA mixtures, or MePDA or an aqueous solution containing BRONCO were prepared according to the methods described above and sprayed onto food surface using a standard hand held air brush Badger model 200, USA). Solutions were thinned or concentrated with their corresponding solvent to achieve desired coating concentrations. Coating was accomplished by applying a steady stream of vaporized material to the surface at a distance of 1–6 inches. Patterns were formed using paper stencils or by careful hand movement. After coatings were applied and allowed to dry, the surfaces were polymerized using a hand held UV lamp (254 nm).

130–150° F. Thermochromic Corn Syrup: Temperature indicating syrup for hot pancakes, waffles, or the like were made using a microcrystalline suspension of a polymeric polydiacetylene. 2 gm 10,12-tricosadiynoic acid was mixed with 45 ml corn syrup (Karo brand Best Foods, Englewood Cliffs, N.J.) and then probe sonicated at 40% power using a 400 watt sonicator (Cole Parmer Instruments, Vernon Hills, Ill.) for 5 minutes. The sample heated to about 140° F. during sonication. After uniform mixing, the sample was allowed to cool to room temperature (3 hours). A white cloudy suspension appeared within 1 hour. The sample was mixed using a stir rod until a creamy consistency resulted. The sample was polymerized to a deep dark blue color in a shallow plastic container using a hand held UV lamp (254 nm, Cole Parmer Instruments, Vernon Hills, Ill.). The sample was irradiated for 4 minutes and mixed using a stir rod.

The dark blue syrup was immediately available for use with hot foods. The syrup could easily be spread on hot toast or waffles. Upon heating, the dark blue syrup turned bright red in color indicating the surface temperature of the hot food it was applied to. The thermochromic transition temperature occurred at between 130° F. to 150° F.

110–130° F. Thermochromic Corn Syrup: Moderate temperature triggering corn syrup was made using the formulation described above and by adding absolute ethanol at 5% by volume. The ethanol was added to a premixed unpolymerized suspension. The suspension and ethanol were mixed to uniformity for 5 minutes at room temperature and polymerized using the identical conditions described above. The thermochromic transition temperature of the polymerized mixture occurred at between 110° F. to 130° F.

Temperature Indicating Thermochromic Icing/Syrup: 5 ml of the MePDA alcohol solution (above) and 10 gm cake icing (Signature Brands, LLC, Ocala, Fla.) were uniformly mixed at room temperature for 10 minutes. Most of the ethanol from the solution evaporated. The resulting creamy paste was chilled to below freezing (−10° F.) and then exposed to a UV lamp (hand held, 254 nm) for 5–10 minutes while remaining chilled. The mixture was churned during exposure to give a uniform blue appearance. The thermochromic icing was temperature triggered by simply raising it above freezing (greater than 50° F.). The icing turned immediately bright red when applied to surfaces exposed to room temperature, directly exposed to room temperature, or touched by directly by hand. Oils contained within the icing helped to facilitate the temperature triggering of the thermochromic agent in the icing. Partially hydrogenated vegetable oils (soybean and cottonseed) are solid in nature at freezing temperatures, keeping the blue polymeric MePDA stable. As the oils melt at above room temperature, the polymeric MePDA is subsequently influenced to transition from a dark blue color to a bright red. The icing was further packaged in air sealed plastic pouches (4 mil, polyethylene) and heat-sealed using a conventional heat sealer. Care was taken not to expose or contact the dark blue frosting to temperatures above freezing. The frosting/syrup could conveniently be extruded onto a pastry surface. During the application, the dark blue color turned immediately bright red due to finger contact with the pouch and exposure to a room temperature surface.

Temperature Indicating Frozen Waffles: Frozen waffles (Eggo brand, Kellogg Company) were removed from their package and immediately sprayed with an alcohol based monomer solution (above). Waffles were coated at 68° F. using a standard airbrush. Patterns were created using the square cells on each waffle. The monomer solution dried immediately on the waffle surface. The monomer-coated waffles were polymerized using a hand held UV lamp (254 nm, 6 inches for 10 to 60 seconds). Radial polymerization gradients were used to increase the level of polymerization from the outer region of the waffle to the center. Increasing the level of polymerization causes a corresponding increase in the final calorimetric temperature transition of the thermochromic agent. The resulting waffles had a dark blue appearance upon polymerization. The patterned thermochromic indicating waffles were conveniently re-stored in the freezer prior to use.

The temperature indicating waffles were toasted using normal instructions on the package. As the waffles were heated, the dark blue color changed to a bright red/orange. The outer portions of dark blue changed color first. As heating continued, the inner portions of blue at the center of the waffles turned color to red/orange last. The color transition was complete when the waffles were fully heated indicating that toasting was complete and the waffles ready to serve.

Thermochromic Graphically Patterned PopTarts: PopTarts (Kellogg Company) were coated with a commercially available sugar glaze and allowed to dry for several hours at room temperature. Edible laminates jet printed (Kopykake, Torrance, Calif.) with either TDA/PDA or MePDA monomer solutions and the Kopyjet ink jet printing system as described above were applied to the glazed PopTart surface. Initially the glaze surfaces were slightly wetted to facilitate the adherence of the edible laminate. Various entertaining patterns were graphically rendered for application on the PopTarts. The monomer printed surfaces were polymerized using a hand held UV lamp (254 nm) at a distance of 3 inches for 5 to 10 seconds depending on the desired level of blue color. TDA/PDA printed/polymerized PopTarts changed color from a dark blue to a bright red/orange when exposed to toaster or microwave temperatures. MePDA printed/polymerized PopTarts changed color from a dark blue to a bright red/orange when exposed to finger touch or above 90° F.

Processed thin sliced cheese: Pre-packaged thin sliced cheese can be printed with the aqueous solution of the thermochromic agent. The solution can be pre-polymerized or in a monomeric form which can be polymerized after printing. The thermochromic agent is absorbed to the cheese surface upon brief drying causing a strong bonding to occur between the thermochromic agent and the surface of the cheese.

A pattern of the American flag was produced on the surface of a thin slice of American cheese (Kraft 2% Milk Reduced Fat Milk Singles). The pattern was painted using a thin brush and a dark blue solution of pre-polymerized BRONCO. The pattern was allowed to dry at room temperature for 5 minutes and the cheese repackaged for storage.

The flag-painted slice was placed on a hamburger while the burger was cooking on a grill. Within 2–3 minutes, the cheese began to melt. During heating and melting, the dark blue flag pattern became bright red. The flag pattern also started to flow and contort as the cheese melted and flowed. The flow process gave rise to an interesting effect simulating the flag waving or moving.

Low Temperature Indicating Marshmallows: Marshmallows were quickly dip coated into the MePDA alcohol solution and allowed to dry at room temperature or below. The monomer dip coated marshmallows were exposed to UV light (hand held lamp, 254 nm) and rotated for uniform polymerization (approximately 2 minutes) until they became dark blue. The marshmallows were stable at room temperature or below (68° F.). They immediately changed to a bright red/orange color upon direct touching, contact with warm fluids, or placing in the presence of an open flame (95° F. or above).

Touch Sensitive Rice Krispie® Treats: Retail Rice Krispie Treats (Kellogg Company) were air brush spray coated using the method described above and an alcoholic solution of MePDA prepared as described above. The Rice Krispie Treats surfaces were inclined at 30 degrees on an open tray and sprayed at a distance of 4 inches using a moderate stream flow from the airbrush. The coatings were allowed to dry for 5 minutes at 65°. Pattern coating was accomplished using an open letter stencil and spraying just beyond the outline of the stencil. Polymerization was accomplished using a hand held UV lamp (254 nm) moved back and forth over the surface for 5 seconds at a distance of 3 inches. The surface immediately became dark blue and could be made to change color to a bright red/orange by finger touch, breathing on the surface, or biting into the surface.

Franks and Hot Dogs: Processed hot dogs can be impregnated with a thermochromic material which turns color when a specific heat is achieved. The material can be patterned such that lettering may indicate the words "HOT DOG" for promotional and advertisement value. Conveniently, an aqueous form of the thermochromic agent is ink jet printed into a pattern representing words of interest. The polymerizable dual chain lipid BRONCO was suspended in water and pre-polymerize with UV light (254 nm) at room temperature to a dark blue ink color. The polymer solution was printed on the side of a retail available hot dog (Hormel or Kraft). The chromic agent can also be printed on the meat product cellulosic casing prior to filling the casing with processed meats and fillers. Casing are typically extruded, processed, and dried prior to filling. Printing on the unfilled casing provides the advantage of printing on a dry solid surface using high speed printing and drying methods with out effecting the foodstuff. Printing on the casing can involve ink jet printing, pad printing, masking, spraying, silk screening, extrusion or the like.

Embedded food bar codes: Embedded thermochromic bar codes produced directly on the side of a pre-baked ham cut. A thermochromic bar code allows a standard bar code and bare code reader to be used as a thermometer device. An alcoholic solution containing TDA/PDA (described above) was sprayed locally on the side of a 1 pound piece of pre-cooked ham (Hormel Company). The ham surface was prepared by damp drying a 1×2 inch region. The region was sprayed at a distance of 3 inches using an airbrush described above. An ultraviolet transmissive photomask with a negative bar code pattern was prepared using a black film thermal transfer printer (Brother) and 8.5×11 inch sheet of 4 mil thick clear polyethylene sheet. The bar code photomask, sized to 0.75 by 1.5 inch, was placed directly over the sprayed region of TDA/PDA. The bars in the code were transmissive to ultraviolet light (254 nm). The bars were selectively exposed using a light shield over certain bars while others were exposed. This method allowed some bars to be polymerized for 100% more time than others did so that the lesser exposed bars would change color a lower temperatures (125° F.) and the more highly exposed bars would change color at higher temperatures (170° F.). The differential temperatures were set so that a bar code reader could read while ham was hot so that the bar code scanner could interpret the disappearance of certain bars (due to the dark blue to red color transition during heating) as being a different code than when it started. The scanner information was converted digitally using a standard computer so that the corresponding computer output could indicate the actual temperature.

Raw egg holding temperature indicator: Eggs were printed with the alcoholic solution containing MeTDA described above. The monomer solution was spot printed using a porous felt pad saturated with the monomer solution. Printing was conducted while the eggs were held at 40° F. The monomer was allowed to dry for 2 minutes and polymerized at using a hand held UV lamp (254 nm) at 40° F. The dark blue printed spot held its color on an egg until the egg was raised to between 55 to 65° F. were the dark blue spot became bright red/orange indicate that the egg was exposed to an excessive holding temperature range. Eggs should be kept at refrigerator temperature during storage due to the potential contamination of Salmonella and the possibility of cell replication at above refrigerator temperatures.

Pharmaceuticals, such as medications,and vitamin pills: Over-the-counter medications can be coated or printed with the thermochromic material as to indicate to the consumer, pharmacist or medical specialist that the drug has been stored at a safe temperature or has been spoiled at a higher temperature. Throat lozenges can incorporate a chromic agent which can tell the consumer that they have an elevated body temperature or fever. Alternatively an aqueous form of the chromic material can be added to a mouth wash/gargle which changes color if the user has a fever. Wording or graphics printed on the side of over-the-counter or prescription drugs can be printed with a low temperature irreversible thermochromic material. The thermochromic agent is used as an indicator that the drug has been maintained at or below room temperature.

Hot Chocolate: Hot chocolate can be made with a combination of dyes including yellow number 6, red number 40, and blue number 1. The blue number 1 can be replaced with the blue polydiacetylenic thermochromic agent. When hot water is added to the mix, the brown color changes to a combination of yellow and red, bringing the brown mix to a bright orange color. Brownie Mix: Brownie mixes can incorporate the blue chromic agent as the blue component of the brown color. Upon baking the brownie mix in the oven, the dark brown mix will become bright orange indicating both an entertaining color change and that the brownies are done and ready to remove from the oven and eat.

Baby Food: Safety concerns to prevent burns to a baby while eating heated baby food, solids or liquids, can be diminished by using a color reversible thermochromic agent combined with the baby food or formula. Initially at room temperature, the solid food or formula would be a darker non-red/orange color. Upon heating the food or formula the thermochromic agent can be induced through a color change, which will revert to the non-red/orange color when the temperature of the food or formula is safe. The thermochromic agent is also effective in indicating regions of the food or formula that may be too hot and should be mixed with the body of the comestible.

It is evident from the above description and results that by using a thermnochromic agent that undergoes a color change at a predetermined transition temperature many applications accrue. The thermochromic composition can be used to ensure that an ingestible has been stored safely, that it has been cooked to a desirable temperature that it has cooled to a desired temperature or solely for entertainment. The thermochromic agent may be applied to a wide variety of ingestibles in a wide variety of manners or incorporated into the ingestible, particularly liquids. The compositions are physiologically safe and may be modified to be appropriate as to a particular temperature transition and compatible with the ingestible.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A solid ingestible comprising:
    a microcrystalline polydiacetylene polymer having a transition temperature in the range of about −10 to 200° C., wherein said polymer is physiologically acceptable and can be consumed with said ingestible, and wherein said polymer changes color from a first color to a second color at said transition temperature, whereby the color of said ingestible is changed.

2. A solid ingestible having a coating comprising:

a microcrystalline polydiacetylene polymer having a transition temperature in the range of about −10 to 200° C., wherein said polymer is physiologically acceptable and can be consumed with said ingestible, and wherein said polymer changes color from a first color to a second color at said transition temperature, whereby the color of said coating is changed.

3. A solid ingestible comprising a microcrystalline polydiacetylene polymer having a transition temperature in the range of about −10 to 200° C. and at least one food dye, whrein said polymer changes color from a first color to a second color at said temperature, wherein the combination of said polymer and said at least one food dye imparts a color different from said first color and said second color to said ingestible, and wherein said polymer is physiologically acceptable and can be consumed with said ingestible.

4. A solid food having an adherent edible coating comprising:

a design formed by a microcrystalline polydiacetylene polymer, wherein said polymer is physiologically acceptable and said adherent coating can be consumed with said solid food, and wherein said polymer changes color from a first color to a second color at a transition temperature whereby said design changes color.

5. A solid material in contact with food, said solid material comprising:

a physiologically acceptable microcrystalline polydiacetylene polymer that undergoes a color change from a first color to a second color at a transition temperature in the range of about −10 to 200° C., whereby the color of said solid material is changed, and wherein said color change of said polymer is reversible.

6. An solid ingestible comprising:

a microcrystalline polydiacetylene polymer, wherein said polymer interpenetrates said ingestible and wherein said polymer undergoes a color change from a first color to a second color in response to a trigger.

7. The solid ingestible according to claim 6, wherein said color change is reversible.

8. A solid ingestible composition comprising;

at least one of a microcrystalline monomeric and a microcrystalline polymeric diacetylenic compound, wherein said diacetylenie compound is physiologically acceptable, and wherein said diacetylenic compound can polymerize to form or is a polydiacetylene that changes color from a first color to a second color in response to a trigger selected from the group consisting of temperature change, pH change, radiation, ionic strength change, mechanical stress, chemical change, solvent change, hydration state, and enzymatic change; and at least one ingestible carrier material, wherein said ingestible carrier material is selected from the group consisting of an aqueous solution, a solvent-based solution, an oil, a lipid, a sugar, a salt, a seasoning, a lectin, an agglutinin, a protein matrix, and a carbohydrate matrix, and wherein said composition is formed by interpenetrating said diacetylenic compound with said carrier material.

9. The ingestible composition according to claim 8, wherein said monomeric diacetylenic compound is dried prior to polymerization.

* * * * *